United States Patent [19]

Mehl

[11] 4,258,032

[45] Mar. 24, 1981

[54] PRESERVATION OF URINE SPECIMENS

[75] Inventor: Jack J. Mehl, Landing, N.J.

[73] Assignee: Becton, Dickinson and Company, Paramus, N.J.

[21] Appl. No.: 3,237

[22] Filed: Jan. 15, 1979

[51] Int. Cl.³ .................... A01N 37/00; A01N 59/14
[52] U.S. Cl. .................................. 424/148; 128/275; 424/317
[58] Field of Search ............................... 424/148, 317

[56] References Cited

U.S. PATENT DOCUMENTS

| 181,024 | 8/1876 | Am Ende | 424/148 |
| 2,460,641 | 2/1949 | Kleiner | 128/214 |
| 4,116,066 | 9/1978 | Mehl et al. | 128/275 |

FOREIGN PATENT DOCUMENTS

| 466791 | 5/1914 | France | 424/148 |
| 355322 | 4/1961 | Switzerland | 424/148 |

OTHER PUBLICATIONS

Sausova et al.; vol. 82, 1975, 13884j.

Primary Examiner—Allen J. Robinson

[57] ABSTRACT

A liquid urine preservative comprised of boric acid and alkali formate dissolved in a bacteriostatic liquid, such as water or glycerine. The preservative may be included in an evacuated container for a urine sample to facilitate taking of correct sample amounts.

15 Claims, 1 Drawing Figure

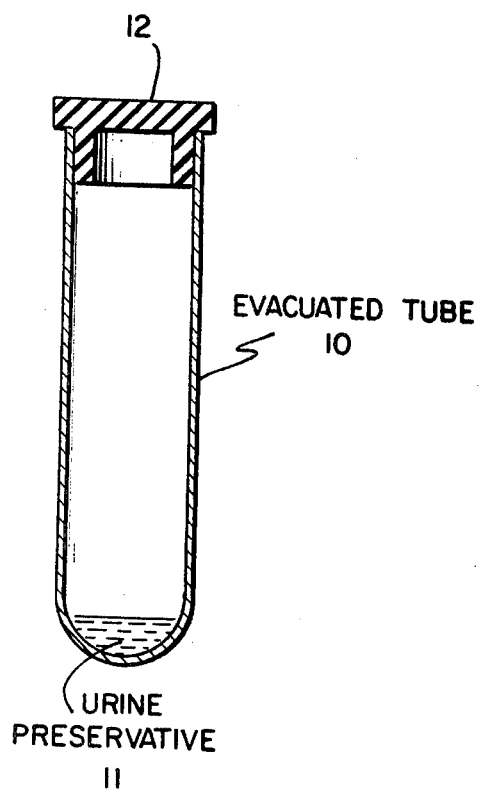

PRESERVATION OF URINE SPECIMENS

This invention relates to the preservation of urine specimens.

Bacterial quantitation of clean-voided urine specimens is employed to determine the presence of urinary tract infection. In many cases, however, such specimens are contaminated from exogenous sources, and in view of the fact that urine has the capability of supporting the proliferation of bacteria, multiplication of such contaminants may occur which will result in false positives. As a result, in order to prevent multiplication of contaminants, culturing or refrigeration of a urine specimen within two to four hours is recommended. In many cases, however, such culturing or refrigeration is not possible, and as a result, there is a need for a preservative for urine specimens which is capable of preserving the urine to prevent multiplication of bacterial contaminants.

Powdered boric acid has been proposed as such a preservative; however, it has been found that such powdered boric acid is toxic to some of the test strains present in the urine. In addition, such powdered boric acid is not effective for preventing proliferation of some bacterial contaminant strains.

As a result, there is a need for an effective preservative for urine specimens.

In accordance with the present invention, there is provided a liquid preservative for urine specimens comprised of boric acid and alkali formate dissolved in a bacteriostatic liquid. Such boric acid and alkali formate are dissolved in the bacteriostatic liquid in an amount effective to preserve a urine specimen. Applicant has found that such a liquid preservative is effective for preserving a urine specimen for a period of at least 24 hours, and in most cases, such preservative is capable of preserving a urine specimen for a period of 48 hours. Thus, applicant has found that the liquid preservative in accordance with the present invention prevents undue proliferation of bacterial contaminants, and is also not unduly toxic to bacteria present in the specimen.

The boric acid is generally present in the liquid preservative in an amount to provide a boric acid concentration in the urine sample in the order of from 0.9 to 1.2 percent. The alkali formate is generally present in the preservative in an amount to provide a formate concentration in the urine sample of from 0.5 to 0.6 percent. The alkali formate is generally either potassium or sodium formate.

The bacteriostatic liquid employed in the preservative is generally either water or glycerine, with glycerine being preferred in that boric acid is more soluble in glycerine, thereby permitting the use of smaller amounts of the total liquid preservative per unit of sample. In addition, it has been found that glycerine interacts with the boric acid and formate to provide for increased preservation; i.e., a liquid preservative in accordance with the invention which includes glycerine as the bacteriostatic liquid has been found to be an effective preservative for a period of 48 hours.

In accordance with a preferred embodiment of the present invention, the liquid preservative is included in a sample container for a urine sample; in particular, an evacuated container, such as an evacuated tube, as described in U.S. Pat. No. 2,460,641. In this manner, the evacuated container includes an amount of liquid preservative effective for preserving the predetermined amount of urine sample which will be drawn into the evacuated sample container. This facilitates handling of the sample, and provides for an effective amount of preservative therefor.

The invention will be further described with respect to the following example; however, the scope of the invention is not to be limited thereby:

EXAMPLE

Urine samples were preserved as follows:

A. Prior Art-Boric Acid

Urine sample containing 1% Boric Acid.

B. Prior Art-Boric Acid

Urine sample containing 1.8% Boric Acid.

C. Present Invention

Boric Acid and sodium formate dissolved in glycerine and added to urine sample to provide 1% boric acid; 0.5% sodium formate; and 10% glycerine in urine.

Each of the preserved urine specimens was tested for its effectiveness against bacteriuria samples by diluting 0.1 ml of the sample with 9.9 ml of sterile distilled water, with 0.1 ml of the diluted sample being transferred to culture plates for count determination after 0, 24 and 48 hours.

The preservation ability is evaluated by determining whether there is an unacceptable rise or drop in the bacterial count, either of which indicates that the preservation is ineffective. The results were as follows:

1. *E. Coli*
Composition A-Unacceptable drop in count after 24 hours.
Composition B-Unacceptable drop in count after 48 hours.
Composition C-Suitable.
2. *C. Freundii*
Composition A-Unacceptable increase in count after 48 hours.
Composition B-Unacceptable drop in count after 24 hours.
Composition C-Suitable.
3. *S. Pyogenes*
Composition A-Unacceptable drop after 24 hours.
Composition B-Unacceptable drop after 24 hours.
Composition C-Suitable.
4. *S. Faecalis*
Composition A-Unacceptable rise after 24 hours.
Composition B-Unacceptable rise after 48 hours.
Composition C-Slight and acceptable rise after 48 hours.
5. *P. Mirabilis*
Composition A-Suitable
Composition B-Unacceptable drop after 48 hours.
Composition C-Suitable.
6. *P. Morgani*
Composition A-Suitable
Composition B-Unacceptable drop after 48 hours.
Composition C-Suitable.
7. *Pseudomonas*
Composition A-Suitable
Composition B-Unacceptable
Composition C-Suitable All three compositions were found to be suitable as a preservative for *E. Cloacae;* and *K. Pneumoniae.*

The composition of the present invention (Composition C) was also found to be comparable to a urine sample preserved by refrigeration over the 24 hours and 48 hour test periods.

A composition in accordance with the invention using water as the bacteriostatic liquid (concentration in urine 1% boric acid; 0.5 sodium formate; 50% water) was found to be an effective preservative in the above tests over the 24 hour period. In some cases, after 48 hours, preservation was not effective.

The present invention is particularly advantageous in that it has been found that by employing the preservative of the present invention for preserving urine samples, the urine preservation is favorably comparable to that obtained by refrigeration. As a result, by proceeding in accordance with the present invention, it is not necessary to effect refrigeration of a urine sample. Moreover, the present invention offers the advantage that urine preservation can be effected with small amounts of preservative, thereby eliminating the necessity of employing a dilution factor in the sample determination. Furthermore, by providing such a preservative in an evacuated container, handling is eased and a correct amount of preservative is added to a predetermined quantity of urine sample. Thus, for example, in accordance with a preferred embodiment, it is possible to employ 0.5 ml of a preservative comprised of boric acid and sodium formate dissolved in glycerine in accordance with the invention in a tube evacuated to draw 5.0 ml of a urine specimen. The preservative is preferably formulated to provide 1% boric acid and 0.5% sodium formate in the urine sample.

As shown in the drawing, in accordance with a preferred embodiment, there is provided an evacuated tube 10 closed by stopper 12, which includes a preservative 11 in accordance with the invention. The preservative 11 is included in an amount to preserve the sample quantity which will be drawn into the tube upon piercing stopper 12. A urine sample can be transferred to tube 10 as known in the art by piercing stopper 12 with a cannula. A sample cup for facilitating such introduction is disclosed in U.S. Application Ser. No. 859,591, filed on Dec. 12, 1977.

These and other advantages should be apparent to those skilled in the art from the teachings herein.

Numerous modifications and variations of the present invention are possible in light of the above teachings and, therefore, within the scope of the appended claims, the invention may be practised otherwise than as particularly described.

I claim:

1. A bacteriostatic liquid preservative for urine, comprising:
    boric acid, alkali formate and a liquid selected from the group consisting of water and glycerine in amounts effective to provide a liquid preservative for a urine sample, said boric acid and alkali formate being dissolved in the liquid to provide from 0.9 to 1.2% of boric acid and from 0.5 to 0.6% of alkali formate in a urine sample.
2. The preservative of claim 1 wherein the liquid is water.
3. The preservative of claim 1 wherein the liquid is glycerine.
4. The preservative of claim 3 wherein the formate is sodium formate.
5. The preservative of claim 4 wherein the boric acid and formate are present in the glycerine in an amount to provide about 1% boric acid, 0.5% sodium formate and 10% glycerine in a urine sample.
6. The preservative of claim 2 wherein the formate is sodium formate.
7. A method for preserving a urine sample, comprising: adding to the urine sample a bacteriostatic liquid preservative comprising boric acid, alkali formate and a liquid selected from the group consisting of water and glycerine in amounts effective to provide a liquid preservative for a urine sample, said boric acid and alkali formate being dissolved in the liquid to provide from 0.9 to 1.2% of boric acid and from 0.5 to 0.6% of alkali formate in a urine sample.
8. The method of claim 7 wherein the bacteriostatic liquid is glycerine.
9. The method of claim 8 wherein the alkali formate is sodium formate.
10. The method of claim 9 wherein the liquid preservative is added to provide 1% boric acid, 0.5% sodium formate and 10% glycerine in the urine sample.
11. The method of claim 10 wherein 0.5 ml of liquid preservative is added to 5.0 ml of urine.
12. The method of claim 7 wherein the bacteriostatic liquid is water.
13. A bacteriostatic liquid preservative for urine consisting essentially of:
    boric acid, alkali formate and a liquid selected from the group consisting of water and glycerine in amounts effective to provide a liquid preservative for a urine sample, said boric acid and alkali formate being dissolved in the liquid to provide from 0.9 to 1.2% of boric acid and from 0.5 to 0.6% of alkali formate in a urine sample.
14. The preservative of claim 13 wherein the liquid is water.
15. The preservative of claim 13 wherein the liquid is glycerine.